United States Patent [19]
Baine et al.

[11] Patent Number: 5,859,266
[45] Date of Patent: Jan. 12, 1999

[54] "N-T-BUTYL-ANDROST-3-5-DIENE-17 β-CARBOXAMIDE-3-CARBOXYLIC" ACID POLYMORPH A

[75] Inventors: Neil Howard Baine, Merion, Pa.; Neville Lewis Holder, Cherry Hill, N.J.; Donald Nathaniel Klein, Phoenixville, Pa.; Robert Lee Webb, West Chester, Pa.; Gary Edward Zuber, Audubon, Pa.

[73] Assignee: SmithKline Beecham Corporation, Philadelphia, Pa.

[21] Appl. No.: 479,871

[22] Filed: Jun. 7, 1995

Related U.S. Application Data

[63] Continuation of Ser. No. 307,680, Dec. 2, 1994, Pat. No. 5,596,109.

[51] Int. Cl.$^6$ .................................. C07J 3/00; C07J 41/00
[52] U.S. Cl. ................................................................ 552/610
[58] Field of Search ............................................... 552/610

[56] References Cited

U.S. PATENT DOCUMENTS 5,017,568  5/1991  Holt et al. .

OTHER PUBLICATIONS

Endocrinology vol. 130, No. 2, pp. 685–694, 1992.
J. Steroid Biochem, vol. 34, Nos 1–6, pp. 571–575, 1989.
J. Med. Chem. vol. 33, pp. 943–950, 1990.
Proc. Natl. Acad. Sci. USA, vol. 89, pp. 10787–10791, Nov. 1992.
Biochemistry, vol. 29, No. 11, pp. 2815–2824, 1990.
Bioorganic Chemistry, vol. 17, pp. 372–376, 1989.
Bioorganic Chemistry, vol. 19, pp. 245–260, 1991.

*Primary Examiner*—Kimberly J. Prior
*Attorney, Agent, or Firm*—Wayne J. Dustman; Charles M. Kinzig; Edward T. Lentz

[57] ABSTRACT

Polymorph "A" a novel polymorphic form of N-t-butyl-androst-3,5-diene-17β-carboxamide-3-carboxylic acid. Novel processes for preparing polymorph "A" are also disclosed.

3 Claims, 2 Drawing Sheets

"N-T-BUTYL-ANDROST-3-5-DIENE-17 β-CARBOXAMIDE-3-CARBOXYLIC" ACID POLYMORPH A

This is a continuation of application Ser. No. 08/307,680, filed Dec. 2, 1994 now U.S. Pat. No. 5,596,109.

The present invention relates to a novel polymorphic form of N-t-butyl-androst-3,5-diene-17β-carboxamide-3-carboxylic acid.

BRIEF DESCRIPTION OF THE DRAWINGS

Figure I is an Infra-red Spectrum of N-t-butyl-androst-3,5-diene-17βcarboxamide-3-17β-carboxylic acid polymorph A.

Figure II is an enhanced FT-IR spectra of the 3399–3501 $cm^{-1}$ region of Polymorph A disclosing the characteristic N-H stretch of Polymorph A.

DETAILED DESCRIPTION OF THE INVENTION

Figure 1:
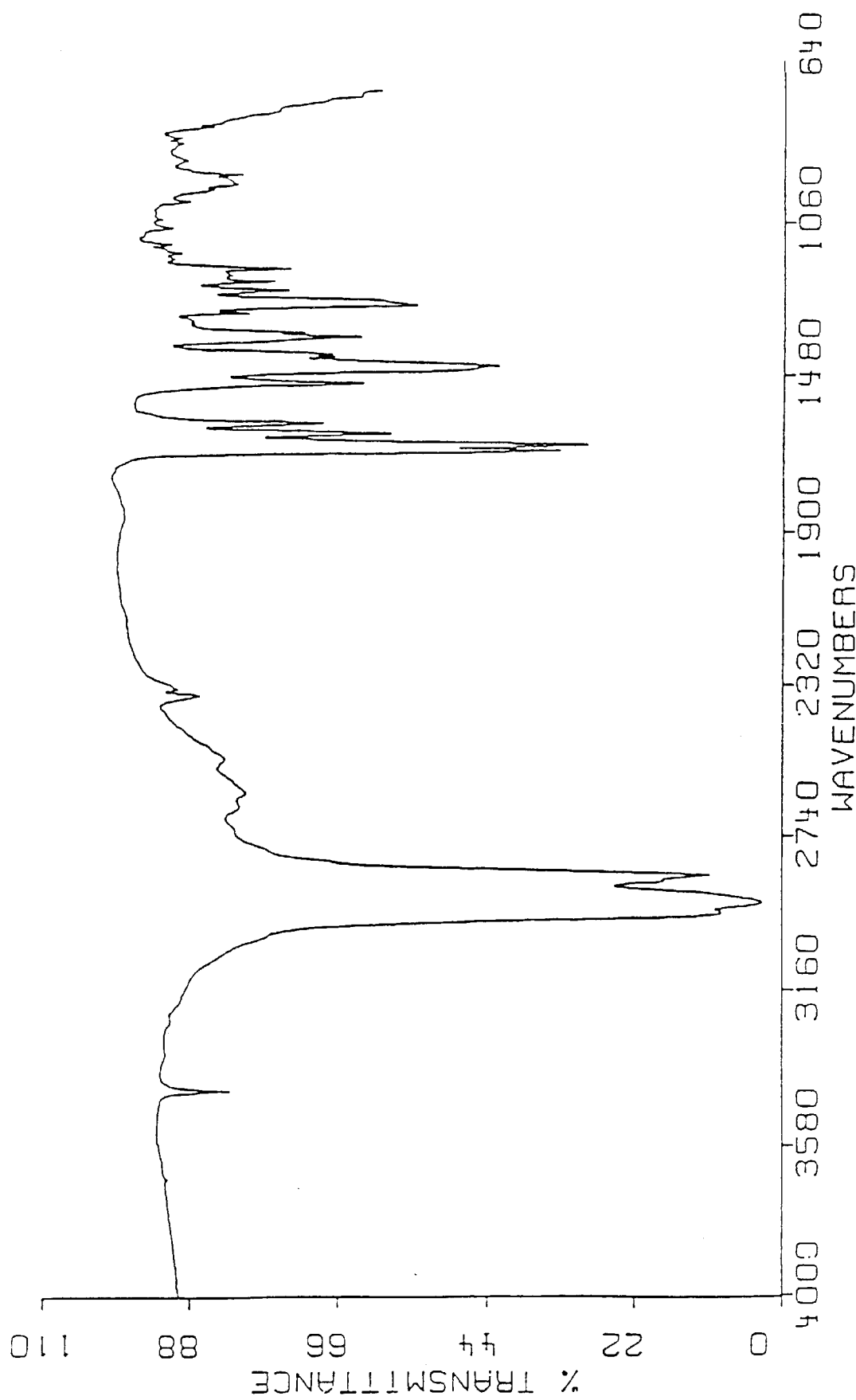

N-t-butyl-androst-3,5-diene-17β-carboxamide-3-carboxylic acid is a compound which is disclosed and claimed as being useful in the treatment of benign prostatic hypertrophy in U.S. Pat. No. 5,017,568, the entire disclosure of which is incorporated by reference. Said compound can be prepared by methods such as described in U.S. Pat. No. 5,017,568. The isolation and identification of the polymorphic forms of said compound is advantageous in identifying desirable physical characteristics of the different crystal forms of said compound.

It has now been found that a polymorphic form (hereinafter Polymorph A) of the compound N-t-butyl-androst-3,5-diene-17β-carboxamide-3-carboxylic acid can be obtained in a high state of polymorphic purity by triturating, by crystallizing or by precipitating said compound from a solvent consisting of or primarily consisting of ethyl acetate or from a solvent consisting of or primarily consisting of t-butyl methyl ether. The substantially pure polymorphic A form of said compound can also obtain by trituration, by crystallization or by precipitation from N-butyl acetate and isopropyl acetate. Contemplated herein is the process of obtaining substantially pure polymorph A from a solvent consisting of or primarily consisting of an organic solvent or a combination of organic solvents which contain an acetate substituent. Also, contemplated herein is the process of obtaining substantially pure polymorph A by trituration, by crystallizing or by precipitating said compound from a solvent consisting of or primarily consisting of an organic solvent which contains an acetate group, preferably ethyl acetate, and t-butyl methyl ether. Typically, a slurry of crude N-t-butyl-androst-3,5-diene-17β-carboxamide-3-carboxylic acid is stirred at above ambient temperature in a solvent consisting primarily of ethyl acetate. Preferably a 12–40% by weight slurry of N-t-butyl-androst-3,5-diene-17β-carboxamide-3-carboxylic acid in ethyl acetate is warmed above ambient temperature, preferably in the range of 65°–70° C., and stirred, preferably for about an hour, followed by filtration which is typically conducted below ambient temperature, preferably in tile range of 0°–5° C. Most preferably said slurry is a 14–20% slurry.

Presently, N-t-butyl-androst-3,5-diene-17β-carboxamide-3-carboxylic acid is known to assume only two polymorphic forms, A and B.

Polymorph A and Polymorph B were individually subjected to intense grinding in a mortar with a pestle for a period of approximately five minutes. Infra-red spectral absorbencies of the post-grinding Polymorph B compound indicated that approximately 5–10% of said polymorph had converted to the Polymorph A form. Infra-red spectral absorbencies of the post-grinding Polymorph A compound indicated retention of polymorphic identity and purity. The above findings indicate that the polymorphic A form of N-t-butyl-androst-3,5-diene-17β-carboxamide-3-carboxylic acid is thermodynamically more stable than the polymorphic B form. The themodynamically more stable polymorphic form of a compound is advantageous for maintaining crystal integrity during manufacture, storing, shipping and handling of solid compositions of said compound. Since, as described above, the polymorphic B form of N-t-butyl-androst-3,5-diene-17β-carboxamide-3-carboxylic acid does not retain its crystal integrity upon grinding and the polymorphic A form retains crystal integrity, Polymorph A is particularly advantageous in the manufacture of tableted forms of N-t-butyl-androst-3,5-diene-17β-carboxamide-3-carboxylic acid.

By the term "crude" as used herein is meant that the isolated N-t-butyl-androst-3,5-diene-17β-carboxamide-3-carboxylic acid starting material exist as an amorphous solid, in an undesired polymorphic form or as a plurality of polymorphic forms.

By the term "N-t-butyl-androst-3,5-diene-17β-carboxamide-3-carboxylic acid" as used herein is meant a compound of the structure

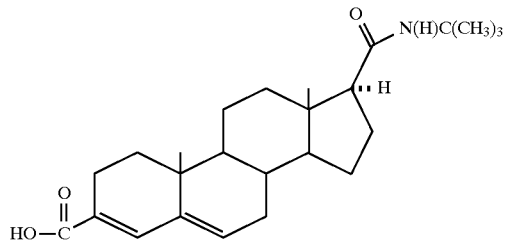

butyl-androst-3,5-diene-17β-carboxamide-3-carobxylic acid polymorph A (prepared by crystallization from ethyl acetate) was analyzed by an X-ray powder diffraction (X-ray diffractometry (XRD) obtained from Micron Incorporated of Wilmington, Del.). The characteristic d-spacings, intensities, and 2-theta values or the diffraction pattern of Polymorph A are listed Table 1 below.

TABLE 1

X-Ray diffraction pattern listing of N-t-butyl-androst-3,5-diene-17β-carboxamide-3-carboxylic acid Polymorph A.

|    | D        | I/IMAX | 2Theta  | PK WIDTH |
|----|----------|--------|---------|----------|
| 1  | 19.12558 | 76.46  | 4.620   | 0.00     |
| 2  | 10.64122 | 2.44   | 8.309   | 0.00     |
| 3  | 9.42222  | 6.60   | 9.386   | 0.00     |
| 4  | 8.72598  | 2.26   | 10.137  | 0.00     |
| 5  | 7.47791  | 12.67  | 11.835  | 0.00     |
| 6  | 6.80494  | 19.00  | 13.010  | 0.00     |
| 7  | 6.14523  | 27.60  | 14.413  | 0.00     |
| 8  | 5.95738  | 47.09  | 14.871  | 0.00     |
| 9  | 5.49032  | 35.12  | 16.144  | 0.00     |
| 10 | 4.91804  | 34.76  | 18.037  | 0.00     |
| 11 | 4.44050  | 25.31  | 19.996  | 0.00     |
| 12 | 4.28147  | 14.11  | 20.746  | 0.00     |
| 13 | 4.09672  | 14.41  | 21.693  | 0.00     |
| 14 | 4.01321  | 19.43  | 22.150  | 0.00     |
| 15 | 3.71622  | 6.71   | 23.946  | 0.00     |
| 16 | 3.47394  | 6.11   | 25.643  | 0.00     |

TABLE 1-continued

X-Ray diffraction pattern listing of N-t-butyl-androst-
3,5-diene-17β-carboxamide-3-carboxylic acid Polymorph A.

|    | D       | I/IMAX | 2Theta | PK WIDTH |
|----|---------|--------|--------|----------|
| 17 | 3.30066 | 4.51   | 27.014 | 0.00     |
| 18 | 3.23171 | 4.04   | 27.602 | 0.00     |
| 19 | 2.75384 | 1.93   | 32.514 | 0.00     |
| 20 | 2.67300 | 2.36   | 33.526 | 0.00     |
| 21 | 2.51415 | 1.96   | 35.713 | 0.00     |
| 22 | 2.20969 | 2.68   | 40.838 | 0.00     |

The following example illustrates preparation of N-t-butyl-androst-3,5-diene-17β-carboxamide-3-carboxylic acid polymorph A. The example is not intended to limit the scope of the invention as defined hereinabove and as claimed below.

EXAMPLE 1

Figure 2:
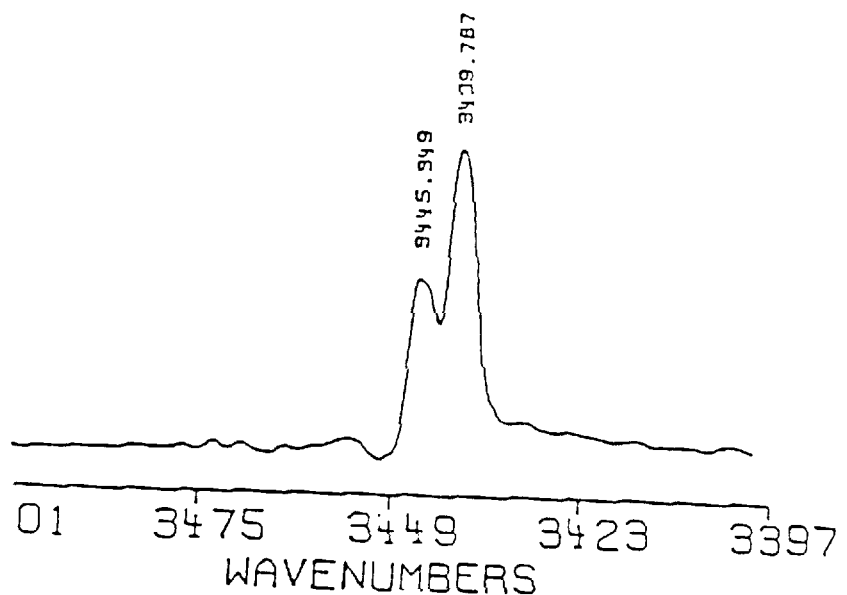

N-t-butyl-androst-3,5-diene-17β-carboxamide-3-carboxylic acid Polymorph A 6.4 g of crude N-t-butyl-androst-3,5-diene-17β-carboxamide-3-carboxylic acid was added to 38.4 ml of ethyl acetate. The resulting slurry was warmed, with stirring, at about 65°–70° C. for about two hours. The resulting slurry was cooled to about 0°–5° C. for 1 hour, and was filtered and washed with 5–10 ml of cold ethyl acetate. The product was filtered dried under vacuum at about 50° C. to afford 5 grams of substantially pure N-t-butyl-androst-3,5-diene-17β-carboxamide-3-carboxylic acid in its polymorph form. The infra-red spectrum of the product is shown in FIGS. 1 and 2.

Infra-red spectral absorbancies of N-t-butyl-androst-3,5-diene-17β-carboxamide-3-carboxylic acid polymorph A (prepared by crystallization from ethyl acetate) were obtained. (spectrum obtained from Nujol (mineral oil) on sodium chloride plates) (apparatus, Nicolet 6000 FT-IR using a mercury cadmium telluride detector, analysis time 7.6 minutes (800 scans), Enhancement Program Nicolet IRDCON).

Characteristic polymorph A form bands occur at 3441 $cm^{-1}$ (N-H stretch); 1678 $cm^{-1}$ (acid C=O stretch); and 1662 $cm^{-1}$ (amide C=O stretch). An FT-IR spectra of polymorph A is shown in FIG. 1 below. The resolution enhanced FT-IR spectra of the 3399–3501 $cm^{-1}$ region disclosing said characteristic N-H stretch of polymorph A is shown in FIG. 2 below.

What is claimed is:

1. A compound of the structure

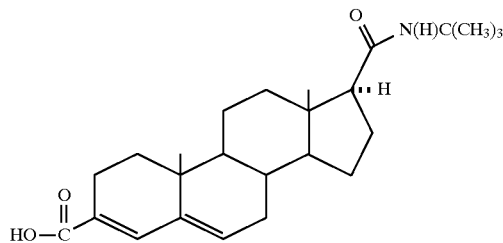

substantially in the polymorph A form.

2. A compound according to claim 1 having the infra-red spectrum as shown in FIG. 1 and the x-ray diffraction pattern listing shown in Table 1.

3. A compound according to claim 1 having the infra-red spectrum as shown in FIG. 2 and the x-ray diffraction pattern listing shown in Table 1.

* * * * *